United States Patent
Lee

(10) Patent No.: US 10,980,630 B1
(45) Date of Patent: *Apr. 20, 2021

(54) CONTACT LENS-BASED METHODS TO DELIVER POWER TO INTRAOCULAR DEVICES

(71) Applicant: Verily Life Sciences LLC

(72) Inventor: Shungneng Lee, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/180,820

(22) Filed: Nov. 5, 2018

Related U.S. Application Data

(63) Continuation of application No. 15/393,837, filed on Dec. 29, 2016, now Pat. No. 10,117,740.

(Continued)

(51) Int. Cl.
*A61F 2/16* (2006.01)
*G02C 7/04* (2006.01)
(Continued)

(52) U.S. Cl.
CPC ............ *A61F 2/1624* (2013.01); *G02C 7/04* (2013.01); *G02C 7/083* (2013.01);
(Continued)

(58) Field of Classification Search
CPC ............ A61F 2/1624; A61F 2250/0001; A61F 2250/0002; B29D 11/026; B29D 11/00826
See application file for complete search history.

(56) References Cited

U.S. PATENT DOCUMENTS

| 5,935,155 | A | 8/1999 | Humayun et al. |
| 2004/0106965 | A1 | 6/2004 | Chow |

(Continued)

FOREIGN PATENT DOCUMENTS

WO 2006015315 A2 2/2006

OTHER PUBLICATIONS

Hayden, A.F., "Electronic IOLs: the future of cataract surgery", Eye World, Feb. 2012.

*Primary Examiner* — David H Willse
*Assistant Examiner* — Javier G Blanco
(74) *Attorney, Agent, or Firm* — McDonnell Boehnen Hulbert & Berghoff LLP

(57) ABSTRACT

An eye-mountable device is provided that includes a battery or other local power source and that can wirelessly power one or more intraocular devices using power from the battery. The eye-mountable device could be provided as a contact lens. The eye-mountable device could provide power to an intraocular device by emitting radio frequency energy, time-varying electrical fields through the conductive medium of the eye, or optical energy. The intraocular device could include an electronic lens configured to provide a controllable optical power to the eye. The intraocular device could include sensors configured to detect accommodation forces exerted by muscles of the eye; such detected forces could be used to control an electronic lens of the intraocular device or an electronic lens of the eye-mountable device. The battery could be rechargeable and the eye-mountable device could be configured to receive power to recharge the battery.

8 Claims, 7 Drawing Sheets

Related U.S. Application Data

(60) Provisional application No. 62/289,220, filed on Jan. 30, 2016.

(51) Int. Cl.
*G02C 7/08* (2006.01)
*B29D 11/02* (2006.01)
*B29D 11/00* (2006.01)

(52) U.S. Cl.
CPC . *A61F 2250/0001* (2013.01); *B29D 11/00038* (2013.01); *B29D 11/00826* (2013.01); *B29D 11/026* (2013.01)

(56) References Cited

U.S. PATENT DOCUMENTS

| | | | |
|---|---|---|---|
| 2006/0271129 A1 | 11/2006 | Tai et al. | |
| 2009/0264966 A1 | 10/2009 | Blum et al. | |
| 2011/0152969 A1 | 6/2011 | Zehnder et al. | |
| 2013/0245754 A1* | 9/2013 | Blum | A61F 2/1627 623/6.13 |
| 2014/0058506 A1* | 2/2014 | Tai | A61F 9/007 623/4.1 |

\* cited by examiner

CONTACT LENS-BASED METHODS TO DELIVER POWER TO INTRAOCULAR DEVICES

CROSS-REFERENCE TO RELATED APPLICATION

This application claims priority to U.S. Provisional Patent Application No. 62/289,220, filed Jan. 30, 2016 and U.S. Non-Provisional patent application Ser. No. 15/393,837, filed Dec. 29, 2016, which are hereby incorporated by reference in their entirety.

BACKGROUND

Unless otherwise indicated herein, the materials described in this section are not prior art to the claims in this application and are not admitted to be prior art by inclusion in this section.

Devices can be provided on the surface of the eye and/or within the eye to provide a variety of functions. In some examples, these functions can include functions to improve the ability of a person to view their environment (e.g., to provide an optical correction, to stimulate the retina directly) and/or to present additional visual information to the person (e.g., to present a heads up display or other indications to the person). Additionally or alternatively, these functions can include detecting a property of the body of a person (e.g., a blood glucose level, a concentration of an ion in the blood) via the eye, e.g., by accessing tears or other fluids that may be accessible on or within the eye and that have some relationship to the property of interest. Such functions can be provided by an external, eye-mountable device (e.g., a contact lens that is configured to detect a glucose level in tear fluid, to provide a static and/or controllable optical power to the eye, to provide light to the retina to indicate some information to a person) and/or by an intraocular device implanted within the eye (e.g., a retinal implant configured to stimulate the retina to restore vision, a device implanted within the lens capsule to provide a static and/or controllable optical power to the eye).

SUMMARY

Some embodiments of the present disclosure provide a system including: (i) a first device that is removably mountable on an eye and that includes a battery and a wireless power transmitter that is operatively coupled to the battery such that the power transmitter can wirelessly transmit power from the battery; and (ii) a second device that is implantable within the eye and that includes a wireless power receiver that can receive power wirelessly transmitted by the wireless power transmitter of the first device when the first device is mounted on the eye and the second device is implanted within the eye.

Some embodiments of the present disclosure provide an eye-mountable device that includes: (i) a battery; and (ii) a wireless power transmitter that is operatively coupled to the battery and that can wirelessly transmit power from the battery to an implanted device when the eye-mountable device is mounted on an eye and the implanted device is implanted within the eye.

Some embodiments of the present disclosure provide a method including: (i) mounting a first device to an eye, wherein the first device includes a battery and a wireless power transmitter, wherein a second device is implanted within the eye and includes a wireless power receiver. The method additionally includes: (ii) wirelessly transmitting power from the battery via the wireless power transmitter; and (iii) receiving, by the wireless power receiver, the power transmitted from the battery via the wireless power transmitter.

These as well as other aspects, advantages, and alternatives, will become apparent to those of ordinary skill in the art by reading the following detailed description, with reference where appropriate to the accompanying drawings.

DETAILED DESCRIPTION

Figure 1A:
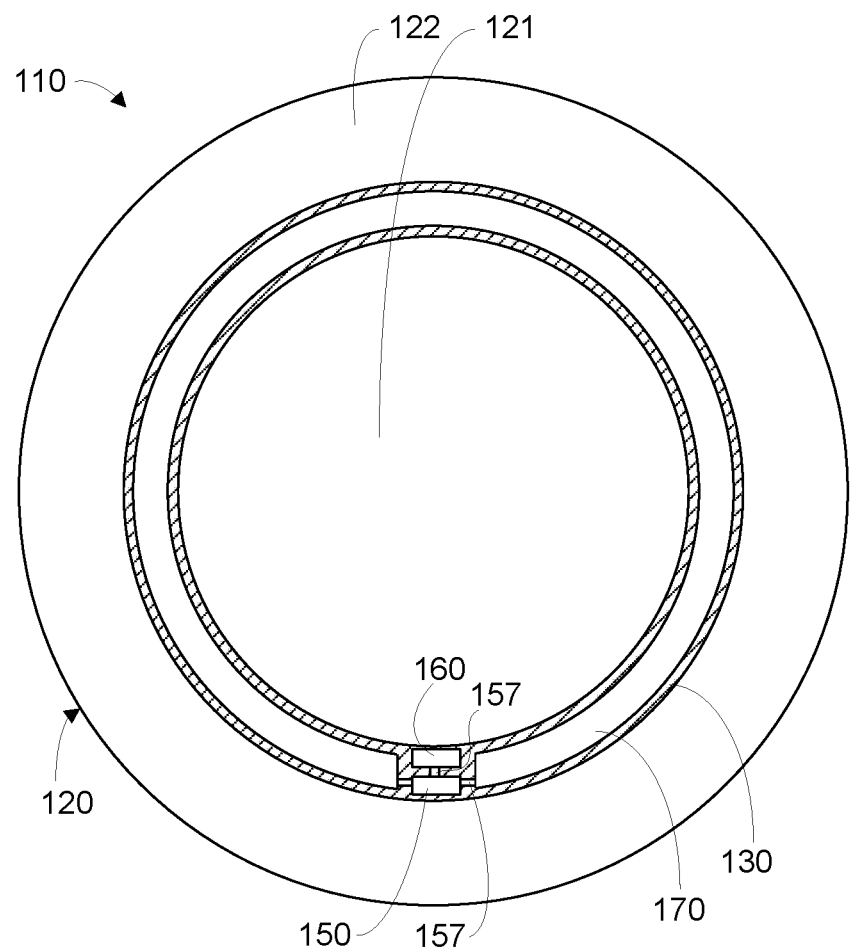
FIG. 1A is a bottom view of an example eye-mountable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Devices located within the human body can operate using power received from a variety of sources. In some examples, wherein the power requirements and/or operational lifetime of the device are sufficiently short, a device could be powered by a battery of the device. For example, a variety of implanted pacemaker devices are powered by batteries that may require replacement after a period of operation of the pacemaker. Additionally or alternatively, a device could receive power from outside of the body. In some examples, this could include a cable extending from the device through the skin such that an external power source may be connected to the cable to power the device. In other examples, the device could receive wireless energy from outside of the body, e.g., using an antenna coil to receive radio frequency electromagnetic energy.

Implanted devices could be located within the eye of a person. Such devices could be located within the lens capsule, within the anterior chamber, within the fibrous wall of the eye, proximate to the retina, or in some other location(s) of the eye according to an application. For example, a device could include an electronically actuated lens and could be located within the lens capsule of the eye (following removal of the natural crystalline lens) to provide a controllable amount of optical power to the eye. Such a device could additionally or alternatively include a sensor operable to detect accommodation forces or other parameters relating to an attempt by the eye to control the optical power of the eye (e.g., to focus on something close to the eye), and such detected parameters could be used to control an actuated lens of the device and/or to transmit an indication of the detected parameters to some other system (e.g., to a contact lens that includes an actuated lens).

Such devices implanted in the eye could be powered by batteries. However, such batteries may require frequent replacement (necessitating a surgical procedure to replace the battery and/or the device). Further, placement of such a power source within the eye could reduce the ability to completely power-off the device (e.g., to reset the device or to deactivate the device). Alternatively, such device implanted in the eye could be powered by energy received wirelessly from outside of the eye. For example, a head mounted display (HMD), eyeglasses, and/or a contact lens could transmit wireless power in a variety of ways that could be received by the implanted device and used to perform functions of the implanted device (e.g., to stimulate the retina, to provide a controllable optical power to the eye, to detect an accommodation force applied to the lens capsule). Further, removal of such external devices from the body and/or disabling the power-transmission functionality of such devices could provide means for resetting the implanted device(s) and/or completely disabling the functionality of the implanted device(s).

In a particular example, a contact lens could be removably mounted to the eye to provide power to a device implanted in the eye. Such a contact lens could include a battery (to provide power for the implanted device and/or to power functions of the contact lens) and a power transmitter that is operable to wirelessly transmit power from the battery to the implanted device. Location of the contact lens on the eye could provide higher-efficiency power transfer to the implanted device (e.g., due to reduced proximity and/or improved alignment with the implanted device relative to an HMD or other power-transmitting device) and/or provide wireless power transfer via means that are available via direct contact with the eye (e.g., via transmission of time-varying electrical currents through the tissue of the eye). Further, embodiment of such a wireless power providing device as an eye-mountable device could provide a relatively cosmetic and/or non-disruptive means for providing power to the implanted device. Such a contact lens could, when the battery is depleted, be removed and replaced by another device having a non-depleted battery and/or recharged to be used again. The contact lens could provide additional functionality, e.g., to provide communications between the implanted device and an external system, to provide a controllable optical power to the eye (using an actuated lens of the contact lens) that is controlled based on accommodation forces detected by the implanted device and transmitted to the contact lens, or some other functionality.

Power could be wirelessly provided, by a contact lens to a device implanted within an eye to which the contact lens is removably mounted, in a variety of ways. In some examples, the power could be transmitted as radio frequency electromagnetic energy, e.g., from a radio-frequency antenna of the contact lens (e.g., a single-turn coil formed from metallic traces disposed on a substrate of the contact lens) to an antenna of the implanted device (e.g., a multi-turn coil formed along the periphery of the implanted device). In another example, the power could be transmitted as optical energy, e.g., from a light-emitting diode (LED) or other light-emitting element(s) of the contact lens to a photovoltaic cell or other light-receiving element(s) of the implanted device. In yet another example, the power could be transmitted as time-varying currents and/or voltages propagating through the tissues and/or fluids of the eye (e.g., through the tears, cornea, vitreous, iris, and/or lens capsule of the eye), e.g., from two or more electrodes of the contact lens to two or more electrodes of the implanted device. The power could be wirelessly transmitted in some other way(s).

II. EXAMPLE EYE-MOUNTABLE DEVICE

An eye-mountable device (e.g., a contact lens) can include a battery and a power transmitter and can be operable to wirelessly transmit, using the power transmitter, power from the battery to an implanted device located on or within an eye when the eye-mountable device is removably mounted to the eye. Such an eye-mountable device could be formed according to one of a variety of shapes such that the eye-mountable device can be removably mounted to an eye, e.g., the eye-mountable device could be shaped to mount to the cornea of the eye, over the pupil and iris. The shape of the eye-mountable device could be specified to facilitate the eye-mountable device being located and/or oriented in a specified way relative to an implanted device within the eye, e.g., to facilitate the location of the eye-mountable device on the cornea over the pupil such that elements (e.g., antennas, light emitters, electrodes) of the eye-mountable device are oriented and/or located relative to elements (e.g., antennas, light receivers, electrodes) of the device implanted in the eye.

Figure 1B:
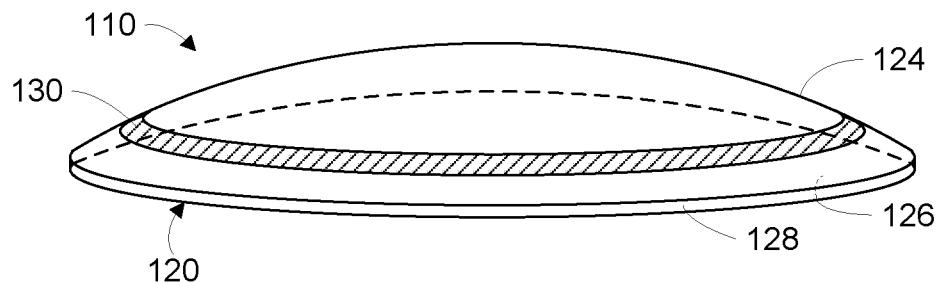
FIG. 1B is an aspect view of the example eye-mountable device shown in FIG. 1A.

FIG. 1A is a bottom view of an example eye-mountable electronic device 110. FIG. 1B is an aspect view of the example eye-mountable electronic device shown in FIG. 1A. It is noted that relative dimensions in FIGS. 1A and 1B are not necessarily to scale, but have been rendered for purposes of explanation only in describing the arrangement of the example eye-mountable electronic device 110. The eye-mountable device 110 is formed of a polymeric material 120 shaped as a curved disk. The polymeric material 120 can be a substantially transparent material to allow incident light to be transmitted to the eye while the eye-mountable device 110 is mounted to the eye. The polymeric material 120 can be a biocompatible material similar to those employed to form vision correction and/or cosmetic contact lenses in optometry, such as polyethylene terephthalate ("PET"), polymethyl methacrylate ("PMMA"), silicone hydrogels, rigid, gas-permeable polymeric materials, combinations of these, etc. The polymeric material 120 can be formed with one side having a concave surface 126 suitable to fit over a corneal surface of an eye. The opposing side of the disk can have a convex surface 124 that does not interfere with eyelid motion while the eye-mountable device 110 is mounted to the eye. A circular outer side edge 128 connects the concave surface 124 and convex surface 126.

The eye-mountable device 110 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 110 can be selected according to the size and/or shape of the corneal surface of the wearer's eye.

The polymeric material 120 can be formed with a curved shape in a variety of ways. For example, techniques similar to those employed to form vision-correction contact lenses, such as heat molding, injection molding, spin casting, etc. can be employed to form the polymeric material 120. While the eye-mountable device 110 is mounted in an eye, the convex surface 124 faces outward to the ambient environment while the concave surface 126 faces inward, toward the corneal surface. The convex surface 124 can therefore be considered an outer, top surface of the eye-mountable device 110 whereas the concave surface 126 can be considered an inner, bottom surface. The "bottom" view shown in FIG. 1A is facing the concave surface 126. From the bottom view shown in FIG. 1A, the outer periphery 122, near the outer circumference of the curved disk is curved out of the page, whereas the center region 121, near the center of the disk is curved into the page.

A substrate 130 is embedded in the polymeric material 120. The substrate 130 can be embedded to be situated along the outer periphery 122 of the polymeric material 120, away from the center region 121. The substrate 130 does not interfere with vision because it is too close to the eye to be in focus and is positioned away from the center region 121 where incident light is transmitted to the eye-sensing portions of the eye. Moreover, the substrate 130 can be formed of a transparent material to further mitigate any effects on visual perception.

The substrate 130 can be shaped as a flat, circular ring (e.g., a disk with a central hole). The flat surface of the substrate 130 (e.g., along the radial width) is a platform for mounting electronics such as chips (e.g., via flip-chip mounting) or batteries and for patterning conductive materials (e.g., via deposition techniques) to form electrodes (e.g., an anode and/or cathode of an electrochemical battery, electrodes of an electrochemical sensor), antenna(e), and/or connections. The substrate 130 and the polymeric material 120 can be approximately cylindrically symmetric about a common central axis. The substrate 130 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 130 can be implemented in a variety of different form factors.

A battery 170, controller 150, and power transmitter 160 are disposed on the embedded substrate 130. The controller 150 can be a chip including logic elements configured to receive power from the battery 170 and to operate the power transmitter 160 to wirelessly transmit power from the battery 170 to an implanted device within an eye to which the eye-mountable device 110 may be removably mounted. The controller 150 is electrically connected to the battery 170 and to the power transmitter 160 by interconnects 157 also situated on the substrate 130. The interconnects 157, elements of the power transmitter 160 (e.g., power transmission electrodes, antennas), and any conductive electrodes (e.g., an anode and cathode of the battery 170, for an electrochemical ion sensor, etc.) can be formed from conductive materials patterned on the substrate 130 by a process for precisely patterning such materials, such as deposition, lithography, etc. The conductive materials patterned on the substrate 130 can be, for example, gold, platinum, palladium, titanium, carbon, aluminum, copper, silver, silver-chloride, conductors formed from noble materials, metals, combinations of these, etc.

As shown in FIG. 1A, which is a view facing the concave surface 126 of the eye-mountable device 110, the battery 170 and power transmitter 160 are mounted to a side of the substrate 130 facing the concave surface 126. However, the electronics, power transmitter, battery, etc. situated on the substrate 130 can be mounted to either the "inward" facing side (e.g., situated closest to the concave surface 126) or the "outward" facing side (e.g., situated closest to the convex surface 124). Moreover, in some embodiments, some electronic components can be mounted on one side of the substrate 130, while other electronic components are mounted to the opposing side, and connections between the two can be made via conductive materials passing through the substrate 130.

The power transmitter 160 illustrated in FIG. 1A is intended as a non-limiting example of the shape, size, relative location (e.g., relative to the controller 150 and/or the battery 170), or other properties of a power transmitter of an eye-mountable device as described herein. The power transmitter 160 could include light-emitting elements (e.g., LEDs, lasers, infrared light sources, visible light sources), electrodes (e.g., electrodes that are operable to inject a time-varying current into a tear fluid such that power may be wirelessly transmitted, via ionic currents or other in-body electrical signals, to electrodes of an implanted device), antennas (e.g., a patch antenna, a loop antenna disposed around the periphery of the substrate 130), or other power-transmitting elements. For example, the power transmitter 160 could include a loop antenna formed on the substrate the at least partially encircle the center region 121 (not shown).

Such a loop antenna can be a layer of conductive material patterned along the flat surface of the substrate to form a flat conductive ring. In some instances, such a loop antenna can be formed without making a complete loop. For instance, such an antenna can have a cutout to allow room for the controller 150 or other elements of the device 110. However, such a loop antenna can also be arranged as a continuous strip of conductive material that wraps entirely around the flat surface of the substrate 130 one or more times. For example, a strip of conductive material with multiple windings can be patterned on the side of the substrate 130 opposite the controller 150 and battery 170. Interconnects between the ends of such a wound antenna (e.g., the antenna leads) can be passed through the substrate 130 to the controller 150. Such a loop antenna could be used to facilitate additional functionality, e.g., to provide means for communicating with other devices (e.g., with an implanted device that is receiving wireless power from the eye-mountable device 110 via the loop antenna and/or via some other means), to provide means for recharging a rechargeable battery of the eye-mountable device 110 (e.g., 170), or to provide some other functionality.

Further, note that the configuration of the battery 170 as a ring disposed on the substrate 130 that partially encircles the center region 121 is intended as a non-limiting example. The battery 170 could completely encircle the center region 170 (e.g., by being formed or disposed on a side of the substrate 130 opposite the controller 130), could take the form of an arc, a square, or could take some other form. The eye-mountable device 110 could include multiple discrete batteries that could be electrically connected in series, in parallel, or according to some other consideration. One or more elements of the battery 170 (e.g., an anode, a cathode) could be formed as conductive traces patterned on the substrate 130. Additionally or alternatively, the battery 170 could be formed independently of the substrate 130 and subsequently disposed on the substrate 130 (e.g., using solder, using an adhesive, by potting the battery 170 and substrate 130 proximate each other in a precursor material used to form the polymeric material 120). The battery could be rechargeable (e.g., could have a lithium-polymer chemistry) or could be non-rechargeable. In some examples, the battery 170 could be activated by exposure to tears or some other aqueous fluid of an eye (e.g., the battery 170 could be a zinc battery that is activated by exposure to an aqueous fluid in which oxygen is dissolved).

Figure 1C:
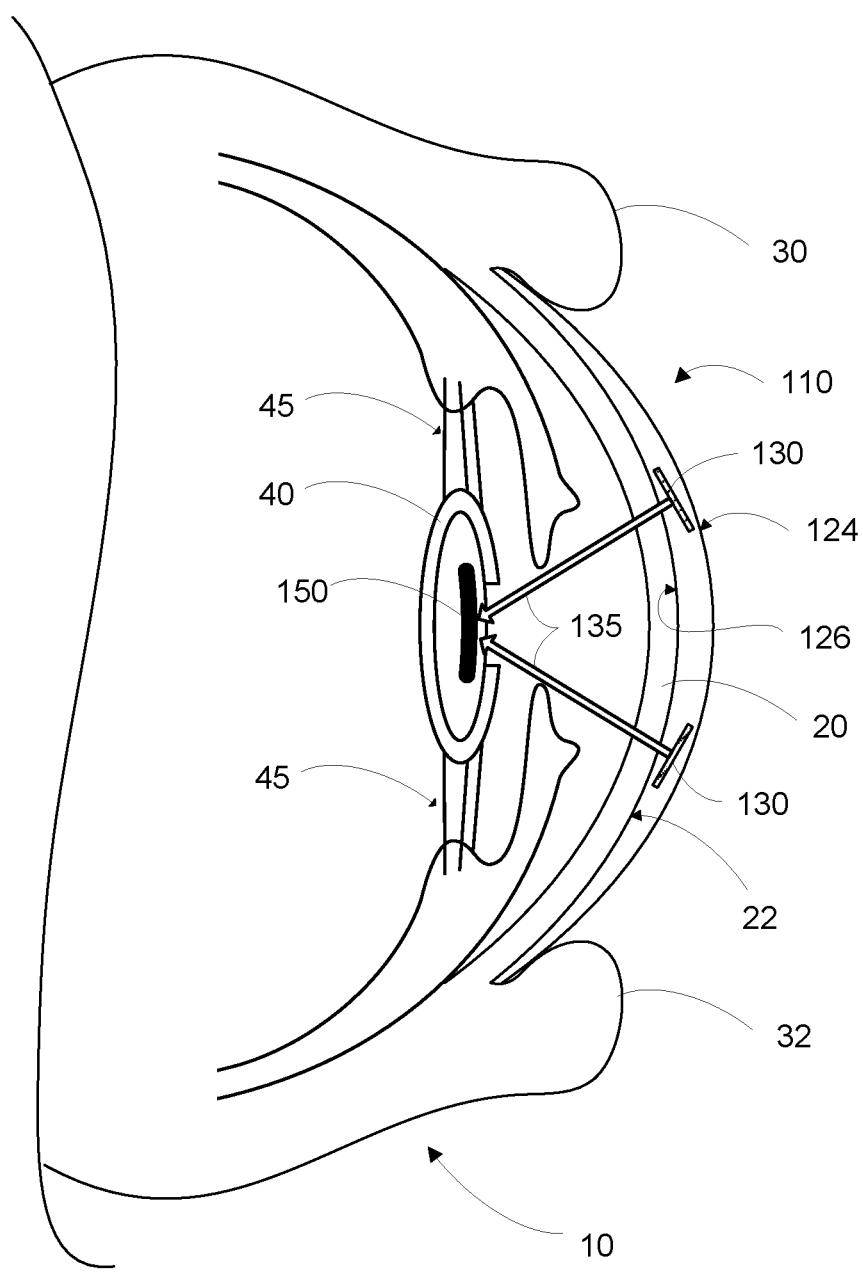
FIG. 1C is a side cross-section view of an example intraocular device located within an eye and the example eye-mountable device shown in FIGS. 1A and 1B while mounted to a corneal surface of the eye.

FIG. 1C is a side cross-section view of the example eye-mountable device 110 while mounted to a corneal surface 22 of an eye 10. An implanted device 150 is located within the eye 10 and is operable to receive wireless power 135 transmitted from the eye-mountable device 110. The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception.

The light received by the retina is transmitted, in the unaltered eye, through the crystalline lens, being refracted by the lens such that light received from elements of an environment (e.g., from a book) arrives in focus at the retina. The crystalline lens is located within the lens capsule of the eye, which is connected, via the zonules, to accommodation muscles and other elements of the eye. Accommodation forces generated by the zonules (e.g., by the accommodation muscles, by intrinsic elasticity of the zonules, or by other sources) act, in the eye, to deform the crystalline lens within the lens capsule, controlling the optical power provided by the crystalline lens.

As shown in FIG. 1C, a window has been formed in the front of the lens capsule 40 of the eye 10 and the crystalline lens has been removed. The implanted device 150 has been disposed within the lens capsule 40 (e.g., is maintained in place within the lens capsule 40 by haptics, by an elastic material disposed and/or formed within the lens capsule 40, or by some other means). Zonules 45 of the eye 10 connect to the lens capsule 40 and exert accommodation forces on the lens capsule 40.

It is noted that relative dimensions in FIG. 1C are not necessarily to scale, but have been rendered for purposes of explanation only in describing the arrangement of the example eye-mountable electronic device 110 and an implanted device 150 located within the eye 10. Further, the location of the implanted device 150 within the lens capsule 40 of the eye 10 is intended as a non-limiting example of the location of a device that is implanted on or within an eye and that is operable to receive wireless power (e.g., from the eye-mountable device 110) and to use such received wireless power to perform some operation(s). An implanted device as described herein could alternatively be located in the anterior chamber, in the vitreous humor, on the surface of the retina, in the posterior chamber anterior to the lens capsule, within the wall of the eye, or at or within some other portion of the eye. Further, such an implanted device could include multiple elements, located, e.g., in multiple different locations. Such multiple elements could be connected via a cable or by some other means. For example, such an implanted device could include a power reception element that is disposed in the posterior capsule and that is operable to receive wireless power from the eye-mountable device 110 and a stimulation element that is disposed on the retina and that is operable to stimulate cells of the retina using power received, via a tether connecting the stimulation element and the power reception element, from the power reception element.

As shown in the cross-sectional view in FIG. 1C, the substrate 130 can be inclined such that the flat mounting surfaces of the substrate 130 are approximately parallel to the adjacent portion of the concave surface 126. As described above, the substrate 130 is a flattened ring with an inward-facing surface (closer to the concave surface 126 of the polymeric material 120) and an outward-facing surface (closer to the convex surface 124). The substrate 130 can have electronic components and/or patterned conductive materials mounted to either or both mounting surfaces. For example, in embodiments wherein the eye-mountable device 110 transmits wireless power 135 by emitting one or more beams of light and/or by injecting time-varying currents via electrodes, light emitting elements (e.g., LEDs, sources of infrared and/or visible light), electrodes, or other power-transmitting elements of a power transmitter of the eye-mountable device 110 could be disposed in the inward-facing surface of the substrate 130. Further, the degree of incline, diameter, or other properties of the substrate 130 and/or the location of elements of a power transmitter or other elements of the eye-mountable device 110 on the substrate 130 could be specified to facilitate power transmission from the eye-mountable device 110 to the implanted device 150. For example, such properties of the eye-mountable device could be specified such that a beam of light emitted from the eye-mountable device is directed toward a power-receiving element (e.g., a photovoltaic cell) of the implanted device 150 when the eye-mountable device 110 is mounted to the eye 10.

The wireless power 135 transmitted, by the transmitter of the eye-mountable device 110, from the battery of the eye-mountable device 110 to a receiver of the implanted device 150 could include light (e.g., beams of light), radio frequency electromagnetic waves, time-varying currents and/or voltages in the tissues and/or fluids of the eye, acoustical waves, electrical fields, magnetic fields, or some other process of propagation of power through space and/or through biological tissues or fluids. As noted above, elements of the power transmitter of the eye-mountable device 110 could be configured such that the elements are aligned with elements of the power receiver of the implantable device 150 when the eye-mountable device 110 is mounted to the eye 10. This could include an alignment that is dependent on the relative orientation of the eye-mountable device on the cornea; in such examples, the eye-mountable device 110 could be weighted or otherwise configured to control the orientation of the eye-mountable device 110 relative to the eye 10 and/or to the implanted device 150. In some examples, elements of the power transmitter and/or power receiver could be radially symmetric, such that power can be transmitted from the eye-mountable device 110 to the implanted device 150 regardless of the orientation of the eye-mountable device 110 relative to the implanted device 150.

Figure 2A:
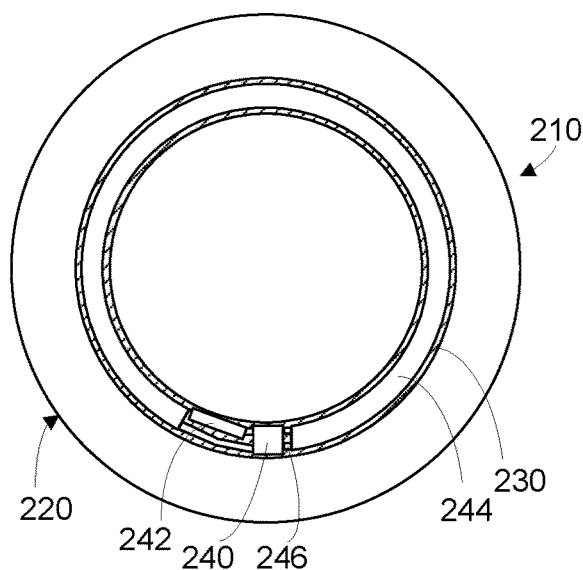
FIG. 2A is a front view of an example eye-mountable device.
Figure 2B:
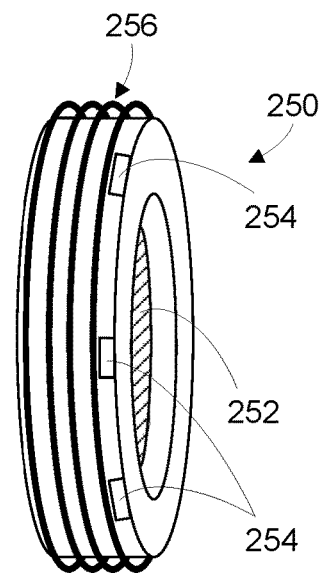
FIG. 2B is a perspective view of an example intraocular device.
Figure 2C:
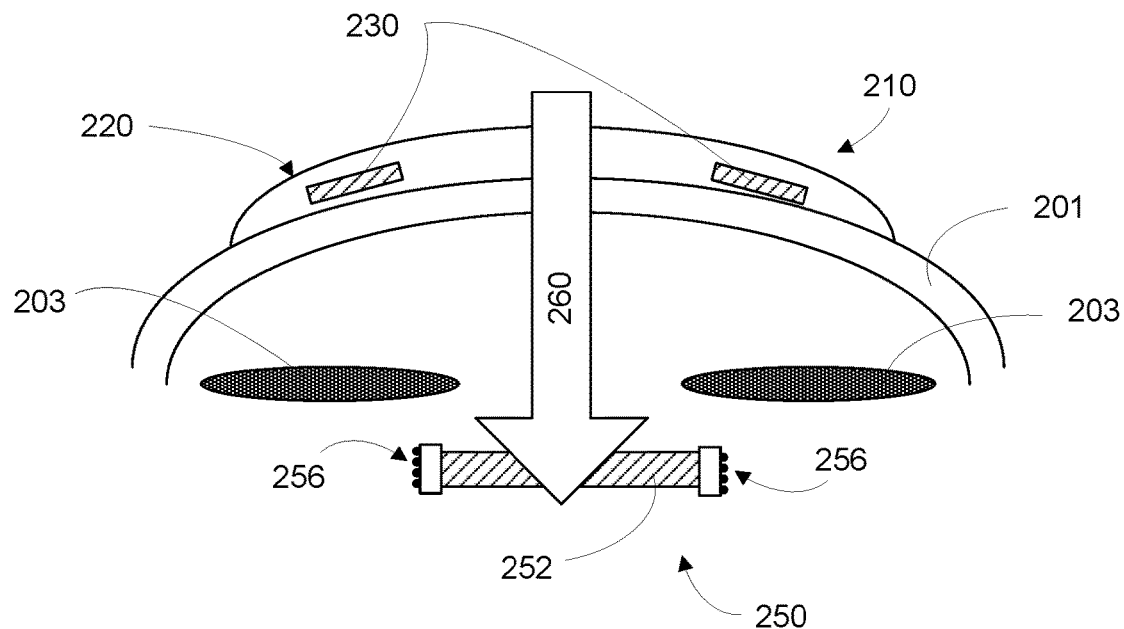
FIG. 2C is a side cross-section view of the example eye-mountable device of FIG. 2A providing wireless power to the example intraocular device of FIG. 2B when the eye-mountable device is mounted to an external surface of the eye and the intraocular device is disposed within the eye.

FIG. 2A shows a top view of an eye-mountable device 210. FIG. 2B shows a perspective view of an implantable device 250 that can be implanted within an eye. The eye-mountable device 210 is removably mountable to an eye and is operable to wirelessly transmit power, from a battery 242 of the eye-mountable device 210, when the eye-mountable device 210 is removably mounted to an eye on or within which the implanted device 250 is implanted. This is illustrated in FIG. 2C, which shows the eye-mountable device 210 mounted to the surface of a cornea 201 of an eye. The implantable device 250 is disposed within the eye, beneath an iris 203 of the eye (e.g., within a lens capsule of the eye). The eye-mountable device 210 is emitting radio frequency electromagnetic energy 260 to provide wireless power to the implanted device 250.

The eye-mountable device 210 includes a substrate 230 disposed within a polymeric material 220 shaped to facilitate mounting of the device 210 to an eye (e.g., to the surface of the cornea 201). A controller 240, a battery 242, and a loop antenna 244 are disposed on the substrate 230 and connected via interconnects 246. The eye-mountable device 210 includes a power transmitter that is configured to emit radio frequency electromagnetic energy. This power transmitter includes the loop antenna 244, elements of the controller 240 (e.g., oscillators, switches, modulators, capacitors, phase locked loops), and any other elements of the device 210 (not shown; e.g., other chips, discrete components, inductors, capacitors, impedance matching structures comprising traces formed on the substrate 230) that are configured to wirelessly transmit power from the battery 242 as radio frequency electromagnetic energy (e.g., as time-varying electromagnetic fields or waves, time-varying magnetic fields, and/or time-varying electric fields).

The implantable device 250 includes a variety of elements (e.g., a housing, an encapsulation layer, haptics) configured to facilitate implantation of the implantable device 250 on or within an eye (e.g., beneath the iris, 203, within a lens capsule, within a wall of the eye, within an anterior chamber of the eye, within or beneath the cornea and/or sclera of the eye). The implantable device 250 additionally includes a multi-turn coil 256 configured to receive radio frequency energy transmitted from the eye-mountable device 210. The implantable device includes a power receiver that is configured to receive radio frequency electromagnetic energy. This power receiver includes the multi-turn coil 256 and any other elements of the implantable device 250 (not shown; e.g., a controller, one or more rectifiers, a lowpass filter, a power storage and/or voltage smoothing capacitor, discrete components, inductors, capacitors, impedance matching structures) that are configured to receive power wirelessly transmitted from the eye-mountable device as radio frequency electromagnetic energy. The implantable device 250 may include further elements, e.g., one or more transmitters and/or receivers configured to communicate with the eye-mountable device 210 or with some other external or implanted system (e.g., by emitting and/or receiving light, radio frequency electromagnetic fields, or other wireless transmissions).

The implantable device 250 further includes elements related to an application of the implantable device 250 to detect accommodation forces generated by an eye (e.g., accommodation forces that are applied to a lens capsule of the eye by zonules of the eye) and to provide a controllable optical power to the eye related to the detected accommodation forces. These elements include accommodation sensors 254 configured to detect the accommodation forces (e.g., by detecting forces or pressures exerted on the sensors 254 via, e.g., haptics of the device (not shown), an elastic material disposed around the device 250 and within the lens capsule, or by some other means) and an actuated lens 252 configured to provide a controllable optical power to an eye (e.g., by applying a voltage to a liquid crystal layer of the actuated lens 252).

Note that, as shown in FIG. 2C, the radio frequency antennas of the eye-mountable device 210 and the implanted device 250 (i.e., the loop antenna 244 and the multi-turn coil 256) are substantially coaxial. That is, the central axis of the radio frequency antennas are in substantially the same direction (e.g., within 15 degrees) and at substantially the same location (e.g., within less than 5 millimeters). The antennas being coaxial could result in an increased efficiency of power transfer between the eye-mountable device 210 and the implanted device 250. As shown, the devices 210, 250 are configured and disposed on/within the eye such that the radio-frequency antennas of the device 210, 250 are coaxial; this includes the devices 210, 250 both being located on a central optical axis of the eye and the radio frequency antennas being substantially coaxial with the central optical axis.

Figure 3A:
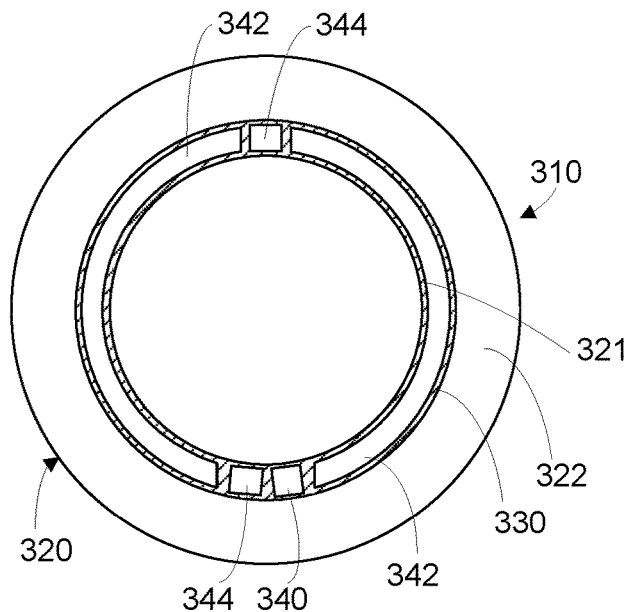
FIG. 3A is a bottom view of an example eye-mountable device.
Figure 3B:
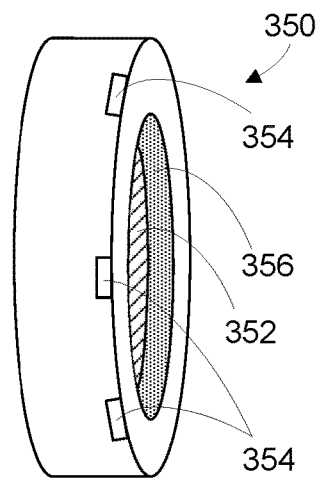
FIG. 3B is a perspective view of an example intraocular device.
Figure 3C:
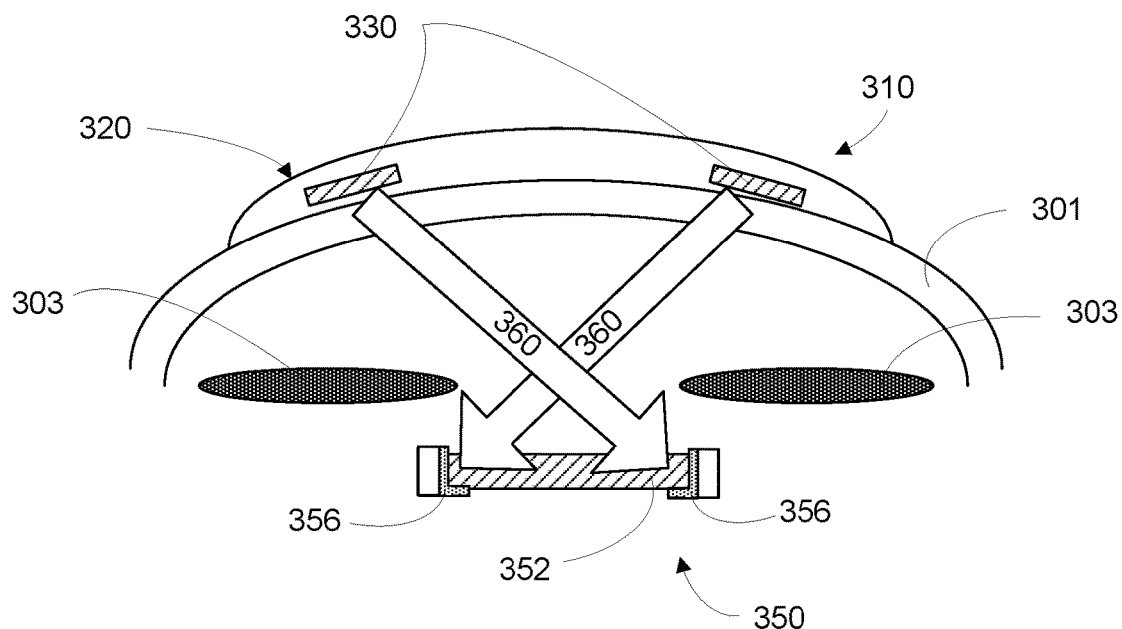
FIG. 3C is a side cross-section view of the example eye-mountable device of FIG. 3A providing wireless power to the example intraocular device of FIG. 3B when the eye-mountable device is mounted to an external surface of the eye and the intraocular device is disposed within the eye.

FIG. 3A shows a bottom view of an eye-mountable device 310. FIG. 3B shows a perspective view of an implantable device 350 that can be implanted within an eye. The eye-mountable device 310 is removably mountable to an eye and is operable to wirelessly transmit power, from a battery 342 of the eye-mountable device 310, when the eye-mountable device 310 is removably mounted to an eye on or within which the implanted device 350 is implanted. This is illustrated in FIG. 3C, which shows the eye-mountable device 310 mounted to the surface of a cornea 301 of an eye. The implantable device 350 is disposed within the eye, beneath an iris 303 of the eye (e.g., within a lens capsule of the eye). The eye-mountable device is emitting light 360 to provide wireless power to the implanted device 350.

The eye-mountable device 310 includes a substrate 330 disposed within a polymeric material 320 shaped to facilitate mounting of the device 310 to an eye (e.g., to the surface of the cornea 301). A controller 340, a battery 342, and light emitters 344 are disposed on the substrate 330 and may be connected via interconnects (not shown). The light emitters 344 could include LEDs, lasers (e.g., VCSELs), emitters of infrared light or other non-visible wavelengths of light, or other light-emitting elements and/or optical elements (e.g., lenses, diffraction grating, collimators, mirrors). The eye-mountable device 310 includes a power transmitter that is configured to emit light. This power transmitter includes the light emitters 344, elements of the controller 340 (e.g., oscillators, switches, modulators, capacitors, phase locked loops, feedback amplifiers, boost and/or buck converters), and any other elements of the device 310 (not shown; e.g., other chips, discrete components, inductors, capacitors, switches) that are configured to wirelessly transmit power from the battery 342 as light (e.g., as beams of light 360).

The emitted light could be infrared light, e.g., to reduce visual artifacts caused by a portion of the emitted light illuminating the retina of the eye.

The implantable device 350 includes a variety of elements (e.g., a housing, an encapsulation layer, haptics) configured to facilitate implantation of the implantable device 350 on or within an eye (e.g., beneath the iris, 303, within a lens capsule, within a wall of the eye, within an anterior chamber of the eye, within or beneath the cornea and/or sclera of the eye). The implantable device 350 additionally includes a light sensor 356 (e.g., one or more photovoltaic cells) configured to receive light transmitted from the eye-mountable device 310. The implantable device includes a power receiver that is configured to receive wireless power transmitted as light. This power receiver includes the light sensor 356 and any other elements of the implantable device 350 (not shown; e.g., a controller, one or more rectifiers, a lowpass filter, a power storage and/or voltage smoothing capacitor, boost converters, buck converters, discrete components, inductors, capacitors) that are configured to receive power wirelessly transmitted from the eye-mountable device as light. The implantable device 350 may include further elements, e.g., one or more transmitters and/or receivers configured to communicate with the eye-mountable device 310 or with some other external or implanted system (e.g., by emitting and/or receiving light, radio frequency electromagnetic fields, or other wireless transmissions).

The implantable device 350 further includes elements related to an application of the implantable device 350 to detect accommodation forces generated by an eye (e.g., accommodation forces that are applied to a lens capsule of the eye by zonules of the eye) and to provide a controllable optical power to the eye related to the detected accommodation forces. These elements include accommodation sensors 354 configured to detect the accommodation forces (e.g., by detecting forces or pressures exerted on the sensors 354 via, e.g., haptics of the device (not shown), an elastic material disposed around the device 350 and within the lens capsule, or by some other means) and an actuated lens 352 configured to provide a controllable optical power to an eye (e.g., by applying a voltage to a liquid crystal layer of the actuated lens 352).

Note that, as shown in FIG. 3C, the light emitters 344 of the eye-mountable device 310 and the light sensor 356 of the implanted device 350 are configured such that beams of light 360 emitted from the eye-mountable device 310 can be received by light sensor 356 despite rotation of the eye-mountable device 310 and further such that the emitted beams of light 360 minimally disperse light toward the rods, cones, or other light-sensitive elements of the eye. In the illustrated example, this includes the light sensor 356 forming a circle such that some aspect of the light sensor 356 received light even if the eye-mountable device 310 rotates (e.g., such that the beams of light 360 rotate about the axis of rotation of the eye-mountable device 310). Additionally or alternatively, the eye-mountable device 310 could be weighted or otherwise configured such that the orientation of the eye-mountable device 310 relative to the implanted device 350 could be controlled. In such an example, the light emitter of the eye-mountable device and the light sensor of the implantable device could be located and/or configured such that, when the weighting of the eye-mountable device aligns the eye-mountable device with the implantable device, a beam of light emitted from the eye-mountable device is received by the light sensor of the implanted device. In another embodiment, the eye-mountable device could include an array of light emitters, each configured to emit a beam of light in a respective direction and/or from a respective location. In such an embodiment, one or more of the light emitters could be selected and used to emit beam(s) of light such that the light emitted from the eye-mountable device is received by a light sensor of the implanted device. The direction of a beam of light emitted from an eye-mountable device could be controlled by some other means, e.g., by an actuated mirror.

The beams of light 360 emitted from the eye-mountable device 310 are, as illustrated in FIG. 3C, off-axis relative to an optical axis of the eye. The eye-mountable device 310 could be configured to provide such off-axis beams of light in order to reduce an amount of light emitted from the eye-mountable device 310 that is not received by light sensor(s) of the implanted device 350 and/or to reduce an amount of light emitted from the eye-mountable device 310 that is absorbed by the retina or other biological elements of the eye, e.g., to reduce visual artifacts caused by such light. Additionally or alternatively, the emitted light could be emitted along the optical axis of the eye, and the implanted device 350 could receive such light (e.g., using a substantially transparent photovoltaic cell disposed on the actuated lens 352 or on some other element(s) of the implanted device 350) and/or could include a filter to block transmission of such light further into the eye (e.g., to prevent transmission of such light to the retina).

Figure 4A:
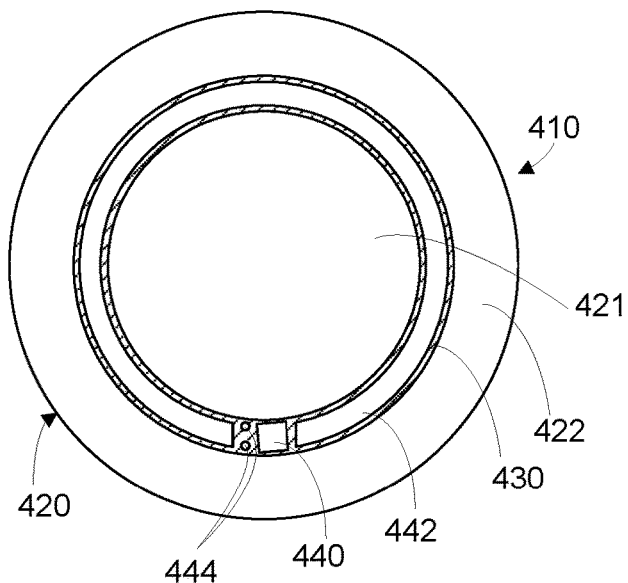
FIG. 4A is a bottom view of an example eye-mountable device.
Figure 4B:
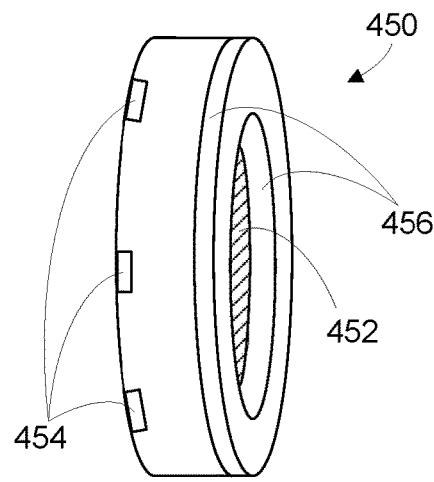
FIG. 4B is a perspective view of an example intraocular device.
Figure 4C:
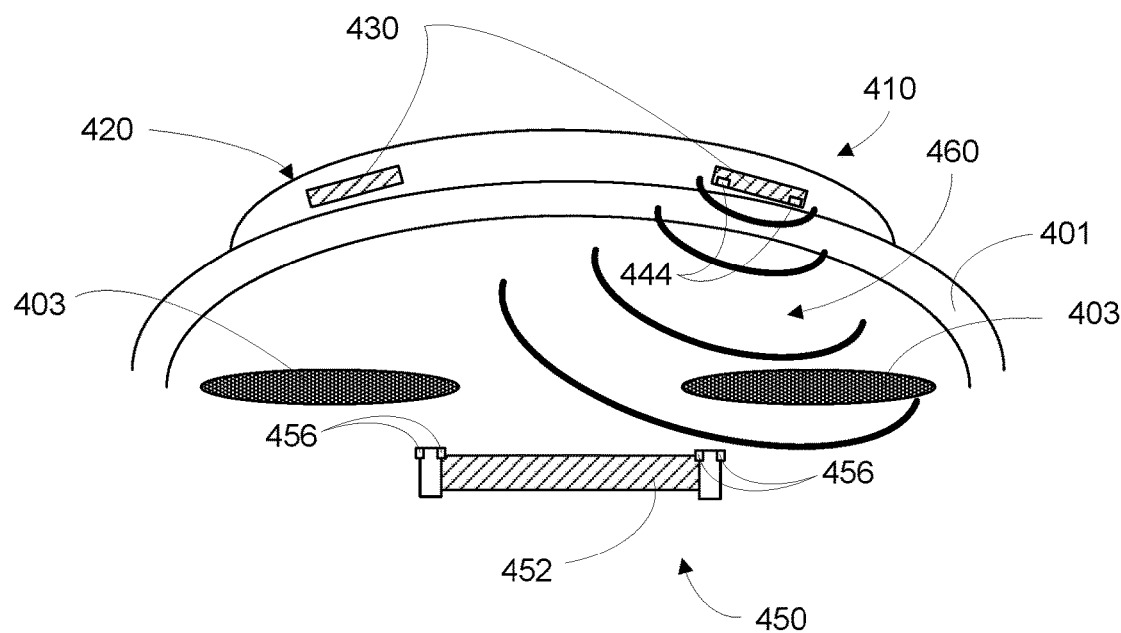
FIG. 4C is a side cross-section view of the example eye-mountable device of FIG. 4A providing wireless power to the example intraocular device of FIG. 4B when the eye-mountable device is mounted to an external surface of the eye and the intraocular device is disposed within the eye.

FIG. 4A shows a top view of an eye-mountable device 410. FIG. 4B shows a perspective view of an implantable device 450 that can be implanted within an eye. The eye-mountable device 410 is removably mountable to an eye and is operable to wirelessly transmit power, from a battery 442 of the eye-mountable device 410, when the eye-mountable device 410 is removably mounted to an eye on or within which the implanted device 450 is implanted. This is illustrated in FIG. 4C, which shows the eye-mountable device 410 mounted to the surface of a cornea 401 of an eye. The implanted able device 450 is disposed within the eye, beneath an iris 403 of the eye (e.g., within a lens capsule of the eye). The eye-mountable device 410 is transmitting time-varying current through electrodes 444 of the eye-mountable device 410 to provide wireless power (via time-varying ionic or other currents within the tissues and/or fluids of the eye) to the implanted device 450.

The eye-mountable device 410 includes a substrate 430 disposed within a polymeric material 420 shaped to facilitate mounting of the device 410 to an eye (e.g., to the surface of the cornea 401). A controller 440, a battery 442, and first-device electrodes 444 are disposed on the substrate 430 and connected via interconnects (not shown). The eye-mountable device 410 includes a power transmitter that is configured to transmit time-varying currents into biological fluids and/or tissues. This power transmitter includes the first-device electrodes 444, elements of the controller 440 (e.g., oscillators, switches, modulators, capacitors, phase locked loops), and any other elements of the device 410 (not shown; e.g., other chips, discrete components, inductors, capacitors) that are configured to wirelessly transmit power from the battery 442 as time-varying currents transmitted through the first-device electrodes 444 (e.g., as time-varying ionic or other currents propagating through the tissues and/or fluids of the eye).

The implantable device 450 includes a variety of elements (e.g., a housing, an encapsulation layer, haptics) configured to facilitate implantation of the implantable device 450 on or within an eye (e.g., beneath the iris, 403, within a lens capsule, within a wall of the eye, within an anterior chamber of the eye, within or beneath the cornea and/or sclera of the eye). The implantable device 450 additionally includes second-device electrodes 456 configured to receive wireless power transmitted as time-varying currents through the tissues and/or fluids of the eye from the eye-mountable device 410. The implantable device includes a power receiver that is configured to receive power from time-varying currents and/or voltages in the tissues and/or fluids of the eye. This power receiver includes the second-device electrodes 456 and any other elements of the implantable device 450 (not shown; e.g., a controller, one or more rectifiers, a lowpass filter, a power storage and/or voltage smoothing capacitor, discrete components, inductors, capacitors, boost converters, buck converters) that are configured to receive power wirelessly transmitted from the eye-mountable device as time-varying currents transmitted into the fluids or tissues of the eye. The implantable device 450 may include further elements, e.g., one or more transmitters and/or receivers configured to communicate with the eye-mountable device 410 or with some other external or implanted system (e.g., by emitting and/or receiving light, radio frequency electromagnetic fields, or other wireless transmissions).

The implantable device 450 further includes elements related to an application of the implantable device 450 to detect accommodation forces generated by an eye (e.g., accommodation forces that are applied to a lens capsule of the eye by zonules of the eye) and to provide a controllable optical power to the eye related to the detected accommodation forces. These elements include accommodation sensors 454 configured to detect the accommodation forces (e.g., by detecting forces or pressures exerted on the sensors 454 via, e.g., haptics of the device (not shown), an elastic material disposed around the device 450 and within the lens capsule, or by some other means) and an actuated lens 452 configured to provide a controllable optical power to an eye (e.g., by applying a voltage to a liquid crystal layer of the actuated lens 452).

Note that, as shown in FIG. 4C, the first-device electrodes 444 of the eye-mountable device 410 and the second-device electrodes 456 of the implanted device 450 are configured such that time-varying voltages and/or currents within the eye, caused by time-varying current transmitted from the eye-mountable device 410 can be received by the second-device electrodes 456 despite rotation of the eye-mountable device 410. In the illustrated example, this includes the second-device electrodes 456 forming circles such that a voltage gradient is present across the second-device electrodes 456 even if the eye-mountable device 410 rotates (e.g., such that the pattern of propagating time-varying currents and/or voltages (e.g., time-varying dipolar electrical fields) rotate about the axis of rotation of the eye-mountable device 410). Additionally or alternatively, the eye-mountable device 410 could be weighted or otherwise configured such that the orientation of the eye-mountable device 410 relative to the implanted device 450 could be controlled.

In such an example, the electrodes of the eye-mountable device and the implantable device could be located and/or configured to increase the distance between the electrodes (e.g., to increase an efficiency of the power transfer and/or to increase a magnitude of a received voltage difference between electrodes of the implanted device). This could include locating electrodes of the eye-mountable device on opposite sides of the eye-mountable device and locating electrodes of the implantable device on opposite sides of the implantable such that, when the weighting of the eye-mountable device aligns the eye-mountable device with the implantable device, the electrodes of the eye-mountable device and the electrodes of the implanted device are aligned. In another embodiment, the eye-mountable device could include an array of electrodes located at respective different locations around the periphery of the substrate 130. In such an embodiment, one or more pairs of the electrodes could be selected and used to emit time-varying currents such that power is received by electrodes located on opposite sides of the implanted device.

Note that the illustrated configurations of the implanted devices 250, 350, 450 (i.e., as disk-shaped devices including the illustrated components) are intended as a non-limiting example embodiment of an implantable device configured to receive wireless power (e.g., from an eye-mountable device) and to perform some operations using such received wireless power. As noted elsewhere herein, such an implantable device could be configured differently according to different applications. Such implanted devices could act to detect physiological properties within the eye (e.g., images, light levels, intraocular pressures, accelerations and/or rotations of the eye) and to transmit wireless indications of such detected properties to systems outside of the eye. In an example, an implantable device could lack an actuated lens and could, instead, include a transmitter configured to transmit a wireless indication (e.g., coded pulses of light, radio frequency waves, and/or currents or voltages within the tissues or fluids of the eye) of a detected accommodation force. In this example, an eye-mountable device could include a receiver configured to receive the wireless indication and could further include an actuated lens that is operable, based on the received indication of the accommodation force and/or based on some other information, to provide a controllable optical power to an eye to which the eye-mountable device is mounted. In some examples, an implantable device as described herein could include a first element configured to be disposed near the anterior surface of the eye (e.g., within and/or beneath the anterior sclera or cornea, within the posterior capsule) and to receive wireless power. The first element could provide such received power, via a cable or other means, to one or more further elements implanted on or within the eye, e.g., to an array of stimulating electrode disposed on the retina.

The eye-mountable devices as shown herein (e.g., 110, 210, 310, 410) could be configured to modulate an intensity, a phase, a frequency, a wavelength, or some other property of the wireless power transmitted by the eye-mountable devices in order to wirelessly transmit information. Conversely, the implantable devices as shown herein (e.g., 150, 250, 350, 450) could include amplifiers, demodulators, decoders, or other elements configured to receive such wirelessly transmitted information. The transmitted information could include commands, programming, detected physiological parameters, or other information that could be used, by the implanted device, to perform some function.

The eye-mountable devices as shown herein (e.g., 110, 210, 310, 410) could include one or more sensors (not shown) configured to detect physiological parameters of a body (e.g., concentrations of analytes in tears or other bodily fluids, an amount of blood in a portion of subsurface vasculature of the sclera or eyelid, an oxygenation state of blood, whether an eyelid is closed), properties of the environment of the device (e.g., an ambient illumination, a barometric pressure, a temperature), properties of the device (e.g., an acceleration, an orientation), or to detect some other information. Such sensors could include accelerometers, electrodes (e.g., electrodes of an electrochemical analyte sensors, electrodes of an electrophysiological sensor configured to detect an electrocardiogram, an electrooculogram, an electromyogram, or some other bioelectrical signal), light detectors, thermometers, gyroscopes, capacitance sensors, pressure sensors, strain gauges, light emitters, microphones, or other elements configured to detect one or more physical variables related to a property of interest. The eye-mountable devices as shown herein could operate such elements to measure physiological parameters or other information of interest at one or more points in time. Such measured properties and/or parameters could be recorded (e.g., in a memory of the device, for example, for later transmission to an external system), transmitted to an external system, indicated using elements of the device (e.g., using a display, using one or more light-emitting elements), used to determine a health state of a user, or used according to some other application.

As noted above, a battery of an eye-mountable device as described herein could be single use (i.e., non-rechargeable) or could be rechargeable. In examples wherein the battery is rechargeable, the eye-mountable device could be configured in a variety of ways to facilitate reception of energy to recharge the battery. The eye-mountable device could include an antenna (e.g., a loop antenna) to receive radio frequency electromagnetic energy, a photovoltaic cell or other light receiving element(s) to receive optical energy, two or more electrodes to receive electrical currents (e.g., via direct contact with corresponding electrodes of a recharger and/or via a conductive fluid in which the eye-mountable device is disposed), or some other means for receiving energy from an external device. In some examples, the means used to receive the energy could have elements in common with the power transmitter used to wirelessly transmit power to an implanted device. For example, a loop antenna used to transmit radio frequency electromagnetic energy from a battery of the eye-mountable device to an implanted device could also be used to receive radio frequency electromagnetic energy to recharge the battery. In another example, electrodes used to transmit time-varying currents from a battery of the eye-mountable device to an implanted device could also be used to receive currents to recharge the battery.

III. EXAMPLE ELECTRONICS OF DEVICES

Figure 5:
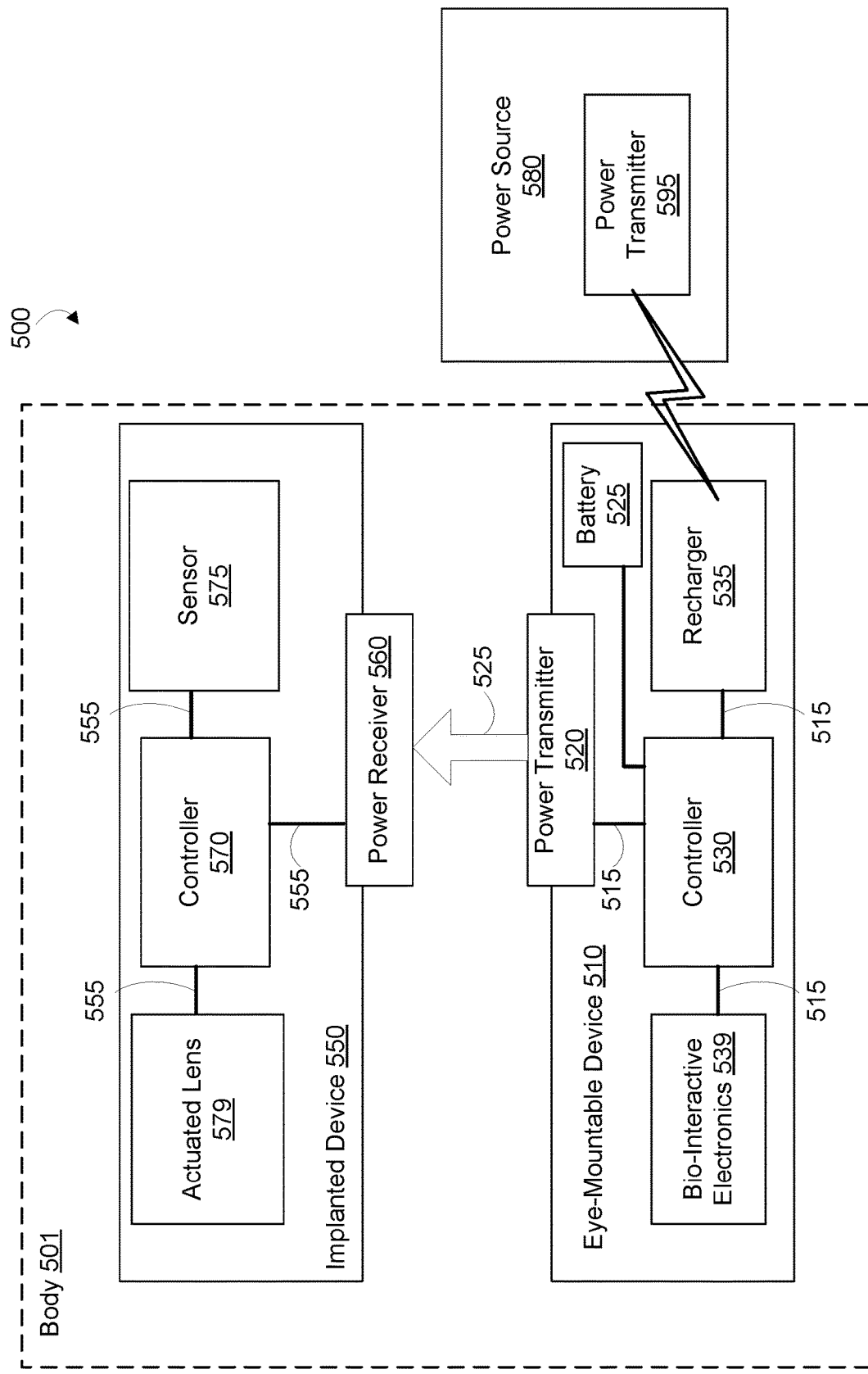
FIG. 5 is a block diagram of an example system that includes an eye-mountable device that can provide power to an intraocular device and that can receive power from a recharger.

FIG. 5 is a block diagram of a system 500 that includes an eye-mountable device 510 wirelessly transmitting power 525 to an implanted device 550. The eye-mountable device 510 may also receive power from a power source 580. As shown indicated by dashed lines in FIG. 5, the implanted device 550 and eye-mountable device 510 are disposed on or within a body 501; specifically, the eye-mountable device is mounted to a surface of an eye of the body 501 and the implanted device 550 is implanted on or within the eye of the body 501. Exposed regions of the eye-mountable device 510 may be made of a polymeric material formed to be contact-mounted to a body surface, e.g. to a corneal surface of the eye.

The eye-mountable device 510 includes a controller 530, bio-interactive electronics 539, a power transmitter 520, a battery 525, and a recharger 535. The bio-interactive electronics 539 are configured to detect physiological properties (e.g., a glucose concentration in tears), to detect movements of the eye and/or eyelids (e.g., to detect command gestures), to provide indications to a user (e.g., by emitting light from an LED and/or display), to provide a controllable optical power to the eye of the body 501 (e.g., by operating an actuated lens) or to otherwise interact with the body 501 and are operated by the controller 530. The power transmitter 520 can be operated to wirelessly transmit power from the battery 525 to the implanted device 550 in the eye. The power transmitter 520 can include light-emitting elements (e.g., LEDs, lasers, VCSELs), radio-frequency electromagnetic energy-transmitting elements (e.g., antennas, coils), elements configured to inject a time-varying current into tissues or fluids of the body 501 (e.g., electrodes), or other elements configured to transmit power from the battery 525 to the implanted device 550. The power transmitter 520, the controller 530, the battery 525, the recharger 535, and the bio-interactive electronics 539 can all be connected together via interconnects 515, e.g., via patterns of metallic traces formed on a substrate material on which the components (e.g., 535, 530, 539) are disposed. Further, the power transmitter 520 could comprise metallic traces or patterns formed on such a substrate material (e.g., to form antennas, impedance matching elements, plates of capacitors, electrodes, mirrors or diffraction gratings).

To facilitate contact-mounting to an eye, a polymeric material of the eye-mountable device 510 can have a concave surface configured to adhere ("mount") to a moistened corneal surface (e.g., by capillary forces with a tear film coating the corneal surface). Additionally or alternatively, the eye-mountable device 510 can be adhered by a vacuum force between the corneal surface and the polymeric material due to the concave curvature. While mounted with the concave surface against the eye, the outward-facing surface of the polymeric material can have a convex curvature that is formed to not interfere with eye-lid motion while the eye-mountable device 510 is mounted to the eye. For example, the polymeric material can be a substantially transparent curved polymeric disk shaped similarly to a contact lens.

The implanted device 550 includes a controller 570, a sensor 575, a power receiver 560, and an actuated lens 579. The power receiver 560 can be operated to receive power wirelessly transmitted, by the power transmitter 520, from the battery 525 of the eye-mountable device 510. This could include receiving optical energy (e.g., via a photovoltaic cell), radio frequency electromagnetic energy (e.g., via an antenna, via a coil), energy from an electrical current or potential in the tissues or fluids surrounding the implanted device 550 (e.g., via electrodes), or receiving some other energy wirelessly transmitted form the eye-mountable device 510. The implanted device 550 could include an ultracapacitor or some other form of short-term energy storage to provide energy for use by the device 550 when power is unavailable from the eye-mountable device 510 (e.g., when the eye-mountable device 510 is not mounted to the eye).

The sensor 575 is configured to detect a physiological property of the body (e.g., a pressure or force, a biopotential, a light intensity). In a particular example, the sensor 575 could be an accommodation sensor configured to detect, directly or indirectly, accommodation forces exerted on a lens capsule of the eye, e.g., by detecting a force or pressure within the lens capsule via haptics, via an elastic material disposed in the lens capsule, via detection of electrical activity of the ciliary muscles, or via some other means.

The actuated lens 579 is operable to control an optical power of the lens 579 that is provided to the eye. Operating the actuated lens 579 to control the optical power of the lens could include applying a voltage to a liquid crystal of the lens 579, applying a voltage to electrowetting elements of the lens 579 or operating a pump or some other element to control a pressure and/or disposition of a fluid within the lens 579, or controlling the optical power of the lens by some other method.

The implanted device 550 and/or eye-mountable device 510 could include additional or alternative elements. In some examples, the implanted device 550 and eye-mountable device 510 could include elements operable to facilitate communication of information between the devices 510, 550. In some examples, this could include the power transmitter 520 being configured to control an intensity, a phase, a frequency, a polarization, a direction, or some other properties of wireless energy transmitted from the power transmitter 520 to indicate information. In a particular example, the actuated lens 579 could be part of the eye-mountable device 510 (that is, the implanted device 550 could lack the actuated lens 579). In this example, the implanted device 550 could include a transmitter and could operate the transmitter to provide wireless indications of an accommodation force detected using the sensor 575. The eye-mountable device 510 could then, using a receiver of the eye-mountable device 510, receive the wireless indications of the accommodation force and use the received information about the accommodation source to control the optical power of the actuated lens of the eye-mountable device 510.

It is noted that the block diagram shown in FIG. 5 is described in connection with functional modules for convenience in description. However, embodiments of the eye-mountable device 510 and/or implanted device 550 can be arranged with one or more of the functional modules ("subsystems") implemented in a single chip, integrated circuit, and/or physical feature. That is, the functional blocks in FIG. 5 need not be implemented as separated modules. Moreover, one or more of the functional modules described in FIG. 5 can be implemented by separately packaged chips electrically connected to one another. Further, note that an eye-mountable device and/or an implanted device as described herein could include additional or alternative components to those shown in FIG. 5 (e.g., additional sensors, actuated lenses, displays, retinal stimulator arrays, electrodes, batteries, controllers, transmitters, receivers, stimulators, etc.). For example, the eye-mountable device 510 could lack the recharger 535 and could be operated as a single-use device (e.g., operated until the battery 525 is depleted and then discarded and/or recycled).

The power source 580 includes a power transmitter 595 to provide power to the eye-mountable device 510 to, e.g., recharge the battery 525 in embodiments wherein the battery 525 is rechargeable. The power source could include a battery (e.g., single-use alkaline batteries, rechargeable lithium-polymer batteries), a solar cell, connection to a mains power source, or some other source of energy. The power transmitter 595 could be configured to provide power wirelessly (e.g., as radio frequency electromagnetic energy via an antenna, as light energy via an LED or other light-emitting element(s)) or through direct contact with the eye-mountable device (e.g., via direct contact between electrodes or other conductive elements of the recharger 595 and corresponding electrodes or other conductive elements of the recharger 535). The power source 580 could be configured to provide power to the eye-mountable device when the eye-mountable device 510 is not mounted to an eye (e.g., when the device 510 is placed within a charging receptacle, on a charging dock, or on or within some other aspect or element of the power source 580) or while the eye-mountable device is mounted to an eye. For example, the power source 580 could be implemented in eye glasses or a head-mounted display and could operate to provide power to the eye-mountable device 510.

IV. EXAMPLE METHODS

Figure 6:
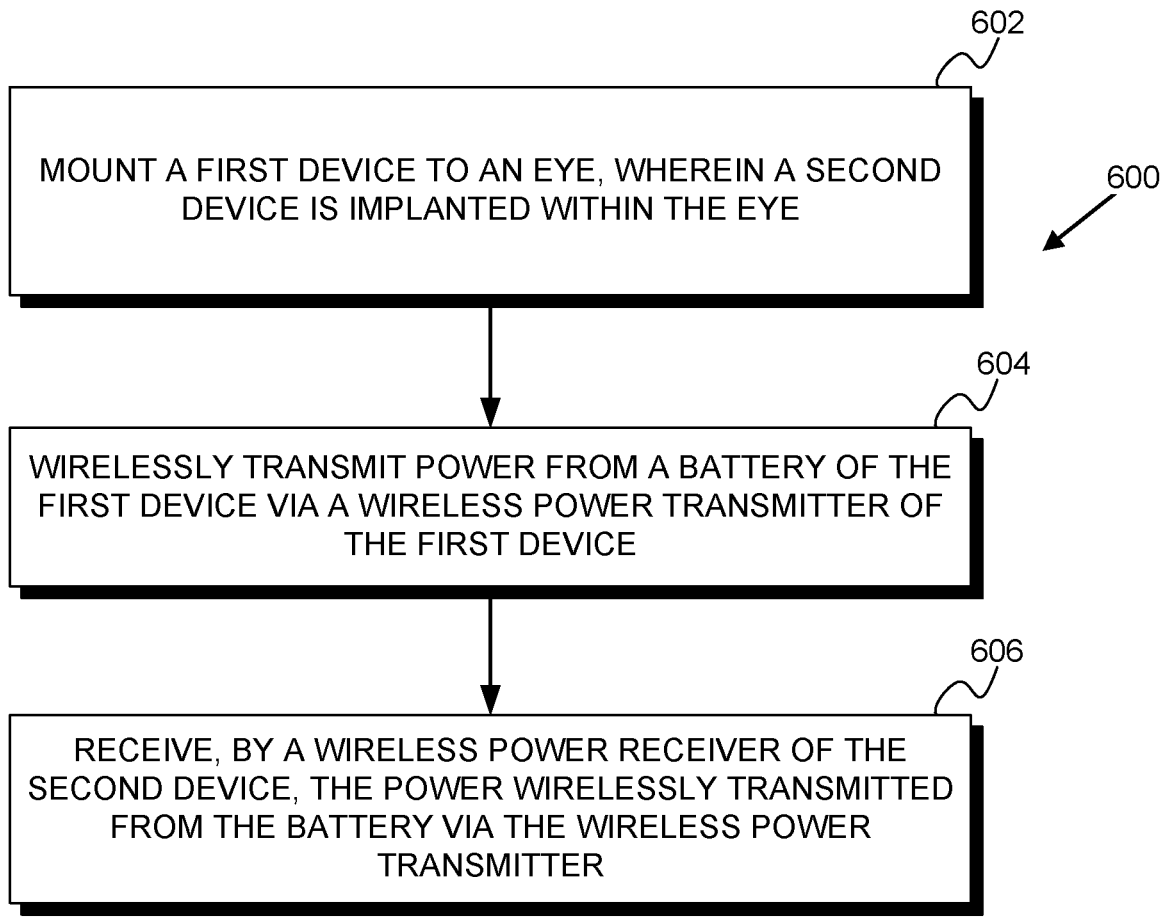
FIG. 6 is a flowchart of an example process.

FIG. 6 is a flowchart of a method 600 for operating a first device to wirelessly transmit power to a second device that is located within an eye (e.g., that is implanted within the eye). The first device includes a battery and a wireless power transmitter and the second device includes a wireless power receiver.

The method 600 includes mounting the first device to an eye, wherein the second device is implanted within the eye (602). In some examples, the first device could be formed to substantially conform to a cornea of the eye, and mounting the first device to an eye (602) could include mounting the first device on the cornea such that the first device is located proximate the second device.

The method 600 includes wirelessly transmitting power from the battery of the first device via the wireless power transmitter of the first device (604). This could include emitting light, e.g., one or more beams of light, from the wireless power transmitter. In another example, this (604) could include emitting, via an antenna, coil, or other elements of the wireless power transmitter, radio frequency electromagnetic energy from the wireless power transmitter. In yet another example, this (604) could include transmitting, via electrodes of the wireless power transmitter, time-varying currents into tissues or fluids of the eye. Wirelessly transmitting power from the battery of the first device (604) could include transmitting energy in some other form (e.g., as acoustical waves). Wirelessly transmitting power from the battery of the first device (604) could include wirelessly transmitting information by modulating an intensity, a phase, a frequency, a wavelength, a direction, a polarization, or some other property of the emitted power in order to wirelessly indicate information to the second device.

The method 600 further includes receiving, by the wireless power receiver of the second device, the power wirelessly transmitted from the battery via the wireless power transmitter (606). This could include receiving light, e.g., one or more beams of light, via a photovoltaic cell or other elements of the wireless power receiver. In another example, this (606) could include receiving, via an antenna, coil, or other elements of the wireless power receiver, radio frequency electromagnetic energy. In yet another example, this (606) could include receiving, via electrodes of the wireless power receiver, time-varying currents and/or potentials from tissues or fluids of the eye. Wirelessly receiving power transmitted from the battery (606) could include receiving wireless energy in some other form (e.g., as acoustical waves). Wirelessly receiving power from the battery of the first device (606) could include wirelessly receiving information form the first device, e.g., by demodulating changes over time of an intensity, a phase, a frequency, a wavelength, a direction, a polarization, or some other property of the received power in order to determine information that has been wirelessly indicated by the first device.

The method 600 could include additional steps or elements in addition to those depicted in FIG. 6 (i.e., 602, 604, 606). For example, the method 600 could include operating the second device to provide some functionality using the power received from the first device. This could include detecting a physiological parameter, e.g., detecting an accommodation force exerted on a lens capsule of the eye. Operating the second device could further include operating an actuated lens of the second device to control, based on the detected accommodation force, an optical power provided by the actuated lens to the eye. In another example, the second device could transmit, using a transmitter of the second device, a wireless indication of the detected physiological parameter. The first device could then receive, using a receiver of the first device, the wireless indication and could perform some operations based on the received indication of the physiological parameter. For example, the indicated physiological parameter could be a detected accommodation force, and the first device could operate an actuated lens of the first device to control, based on the indicated accommodation force, an optical power provided by the actuated lens to the eye. In another example, the method 600 could include operating the first device to receive power and to use the received power to recharge the battery. Other steps or elements of the method 600 are anticipated.

V. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures. Further, note that while example embodiments of intraocular devices (e.g., retinal implants, intraocular lenses) are provided that receive wireless power from a battery-containing contact lens or other battery-containing eye-mountable device, further devices that are configured to be disposed within an eye and to receive power from eye-mountable devices disposed on the surface of the eye are anticipated. Further, multiple such devices could be disposed on and/or within an eye and may wirelessly receive power from an eye mountable device that includes a battery as described herein.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
    a contact lens, wherein the contact lens is removably mountable on an eye and comprises:
        a center region that is configured to cover a pupil of the eye and comprises a transparent material that allows light that is incident on the contact lens to be transmitted to the eye;
        a battery, wherein the battery is disposed within the contact lens outside of the center region; and
        a wireless power transmitter operatively coupled to the battery, such that the wireless power transmitter can wirelessly transmit power from the battery, the wireless power transmitter being one of a plurality of electrodes, a light emitter, or a radio frequency (RF) transmitting antenna; and
    an intraocular lens (IOL), wherein the intraocular lens is implantable within the eye and comprises:
        a wireless power receiver, wherein the wireless power receiver can receive power wirelessly transmitted by the wireless power transmitter of the contact lens when the contact lens is mounted on the eye and the intraocular lens is implanted within the eye, the wireless power receiver being one of a plurality of electrodes, a light sensor, or a radio frequency (RF) receiving antenna;
        an actuated dynamic lens; and
        a controller coupled to the actuated dynamic lens to control an optical power of the actuated dynamic lens.

2. The system of claim 1, wherein the intraocular lens additionally comprises an accommodation sensor that can detect an attempt by the eye to control an optical power of the eye, wherein the controller of the intraocular lens is configured to operate the accommodation sensor to detect an attempt by the eye to control an optical power of the eye, wherein the controller is additionally configured to control the optical power of the actuated dynamic lens based on the detected attempted accommodation by the eye.

3. The system of claim 2, wherein the accommodation sensor is configured to detect accommodation forces applied to a lens capsule of the eye.

4. The system of claim 1, wherein the wireless power transmitter comprises a plurality of first contact lens electrodes, and wherein the wireless power receiver comprises a plurality of intraocular lens electrodes.

5. The system of claim 1, wherein the wireless power transmitter comprises a light emitter, and wherein the wireless power receiver comprises a light sensor.

6. The system of claim 5, wherein the light emitter emits a beam of light that is off-axis relative to an optical axis of the eye when the contact lens is mounted to the eye.

7. The system of claim 1, wherein the wireless power transmitter comprises a contact lens antenna for transmitting radio frequency electromagnetic energy, and wherein the wireless power receiver comprises an intraocular lens antenna for receiving the transmitted radio frequency electromagnetic energy.

8. The system of claim 7, wherein the contact lens antenna and the intraocular lens antenna are substantially coaxial when the contact lens is mounted to the eye and the intraocular lens is implanted within the eye.

\* \* \* \* \*